(12) United States Patent
Hein et al.

(10) Patent No.: US 10,782,114 B2
(45) Date of Patent: Sep. 22, 2020

(54) HYBRID NAVIGATION SENSOR

(71) Applicant: Boston Scientific Scimed Inc., Maple Grove, MN (US)

(72) Inventors: Matthew Hein, Eden Prairie, MN (US); Daniel J. Foster, Lino Lakes, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 352 days.

(21) Appl. No.: 15/846,846

(22) Filed: Dec. 19, 2017

(65) Prior Publication Data

US 2018/0172420 A1 Jun. 21, 2018

Related U.S. Application Data

(60) Provisional application No. 62/436,422, filed on Dec. 20, 2016.

(51) Int. Cl.
*G01B 7/00* (2006.01)
*G01R 33/00* (2006.01)
(Continued)

(52) U.S. Cl.
CPC .............. *G01B 7/003* (2013.01); *A61B 5/062* (2013.01); *A61B 34/20* (2016.02);
(Continued)

(58) Field of Classification Search
CPC ................ G01B 7/003; G01R 33/0094; G01R 33/0011; G01R 33/09; G01R 33/096;
(Continued)

(56) References Cited

U.S. PATENT DOCUMENTS 5,644,230 A   7/1997  Pant et al.
5,994,989 A *  11/1999  Rowe ..................... H01R 31/08
                                                            335/18
(Continued)

FOREIGN PATENT DOCUMENTS

EP         0696357 B1   2/1996
WO      1995009562 A1   4/1995
(Continued)

OTHER PUBLICATIONS

International Search Report and Written Opinion issued in PCT/US2017/067111, dated May 8, 2018, 19 pages.
(Continued)

*Primary Examiner* — Daniel R Miller
(74) *Attorney, Agent, or Firm* — Faegre Drinker Biddle & Reath LLP

(57) ABSTRACT

A sensor assembly includes a first magnetic field sensor that is a first type of sensor and has a first magnetic field sensitivity in a first primary sensing direction. The first primary sensing direction is along a longitudinal axis of the sensor assembly. The sensor assembly further includes a second magnetic field sensor that is a second type of sensor different than the first type of sensor and has a second magnetic field sensitivity in a second primary sensing direction that is less than the first magnetic field sensitivity. The second primary sensing direction is along a second axis that is different than the longitudinal axis.

18 Claims, 3 Drawing Sheets

(51) Int. Cl.
  *G01R 33/09* (2006.01)
  *G01R 33/06* (2006.01)
  *G01R 33/07* (2006.01)
  *A61B 34/20* (2016.01)
  *A61B 5/06* (2006.01)
  *A61B 90/00* (2016.01)

(52) U.S. Cl.
  CPC ...... *G01R 33/0011* (2013.01); *G01R 33/0094* (2013.01); *G01R 33/063* (2013.01); *G01R 33/07* (2013.01); *G01R 33/075* (2013.01); *G01R 33/09* (2013.01); *G01R 33/093* (2013.01); *G01R 33/095* (2013.01); *G01R 33/096* (2013.01); *A61B 2034/2051* (2016.02); *A61B 2034/2053* (2016.02); *A61B 2090/397* (2016.02)

(58) Field of Classification Search
  CPC .... G01R 33/063; G01R 33/07; G01R 33/095; G01R 33/075; G01R 33/093; A61B 34/20; A61B 5/062; A61B 2034/2051; A61B 2090/397; A61B 2034/2053
  See application file for complete search history.

(56) References Cited

U.S. PATENT DOCUMENTS

| | | | |
|---|---|---|---|
| 6,169,254 B1 | 1/2001 | Pant et al. | |
| 6,183,889 B1* | 2/2001 | Koshiba | B82Y 10/00 428/812 |
| 6,184,680 B1 | 2/2001 | Shinoura et al. | |
| 6,273,322 B1* | 8/2001 | Yamamoto | B23K 20/10 228/110.1 |
| 6,484,118 B1 | 11/2002 | Govari | |
| 6,536,123 B2 | 3/2003 | Tamura | |
| 6,593,884 B1 | 7/2003 | Gilboa et al. | |
| 6,690,963 B2 | 2/2004 | Ben-Haim et al. | |
| 6,836,971 B1* | 1/2005 | Wan | G01C 17/38 33/356 |
| 7,301,332 B2 | 11/2007 | Govari et al. | |
| 7,870,678 B2 | 1/2011 | Kwon et al. | |
| 8,390,279 B2 | 3/2013 | Klocke et al. | |
| 8,391,952 B2 | 3/2013 | Anderson | |
| 8,750,961 B1 | 6/2014 | Ries et al. | |
| 9,002,675 B2 | 4/2015 | McIntyre et al. | |
| 2003/0231098 A1 | 12/2003 | Wan | |
| 2004/0124835 A1* | 7/2004 | Kimura | G01R 33/02 324/249 |
| 2007/0080682 A1 | 4/2007 | Govari et al. | |
| 2007/0200564 A1* | 8/2007 | Motz | G01R 33/09 324/247 |
| 2007/0260139 A1* | 11/2007 | Minai | A61B 1/00036 600/420 |
| 2008/0052931 A1 | 3/2008 | Kwon et al. | |
| 2008/0052932 A1* | 3/2008 | Xue | G01C 17/28 33/356 |
| 2010/0171492 A1 | 7/2010 | Klocke et al. | |
| 2011/0234218 A1 | 9/2011 | Lagouge | |
| 2011/0248706 A1 | 10/2011 | Davis et al. | |
| 2012/0081111 A1* | 4/2012 | Kim | G01R 33/091 324/252 |
| 2012/0153942 A1* | 6/2012 | van Veldhoven | G01R 33/0017 324/239 |
| 2012/0299587 A1 | 11/2012 | Rieger et al. | |
| 2013/0127454 A1 | 5/2013 | Ungaretti et al. | |
| 2013/0169272 A1 | 7/2013 | Eichler et al. | |
| 2014/0276004 A1 | 9/2014 | Strupeck et al. | |
| 2014/0327437 A1* | 11/2014 | Han | G01R 19/32 324/252 |
| 2015/0087921 A1 | 3/2015 | Felix et al. | |
| 2016/0245877 A1* | 8/2016 | Deak | G01R 33/093 |
| 2017/0021172 A1 | 1/2017 | Perez et al. | |
| 2017/0059361 A1 | 3/2017 | Nagarkar et al. | |
| 2017/0325715 A1 | 11/2017 | Mehendale et al. | |
| 2018/0042518 A1 | 2/2018 | Fruci et al. | |
| 2018/0153436 A1 | 6/2018 | Olson | |
| 2018/0168482 A1 | 6/2018 | Hein | |
| 2018/0172865 A1 | 6/2018 | Hein et al. | |
| 2018/0220928 A1 | 8/2018 | Blood et al. | |
| 2018/0220929 A1 | 8/2018 | Blood et al. | |

FOREIGN PATENT DOCUMENTS

| | | |
|---|---|---|
| WO | 2014207738 A1 | 12/2014 |
| WO | 2016087970 A1 | 6/2016 |
| WO | 2016196985 A1 | 12/2016 |

OTHER PUBLICATIONS

International Search Report and Written Opinion issued in PCT/US2018/016895, dated Apr. 13, 2018, 11 pages.
International Search Report and Written Opinion issued in PCT/US2018016876, dated Apr. 11, 2018, 10 pages.
PCT Invitation to Pay Additional Fees issued in PCT/US2017067111, dated Mar. 15, 2018, 16 pages.
International Preliminary Report on Patentability issued in PCT/US2017/067111, dated Jul. 4, 2019, 14 pages.
International Preliminary Report on Patentability issued in PCT/US2018/016876, dated Aug. 15, 2019, 7 pages.
International Preliminary Report on Patentablity issued in PCT/US2018/016895, dated Aug. 15, 2019, 7 pages.

* cited by examiner

HYBRID NAVIGATION SENSOR

CROSS-REFERENCE TO RELATED APPLICATION

This application claims priority to Provisional Application No. 62/436,422, filed Dec. 20, 2016, which is herein incorporated by reference in its entirety.

TECHNICAL FIELD

The present disclosure relates to systems, methods, and devices for tracking items. More specifically, the disclosure relates to systems, methods, and devices for electro-magnetically tracking medical devices used in medical procedures.

BACKGROUND

A variety of systems, methods, and devices can be used to track medical devices. Tracking systems can use externally generated magnetic fields that are sensed by at least one tracking sensor in the tracked medical device. The externally generated magnetic fields provide a fixed frame of reference, and the tracking sensor senses the magnetic fields to determine the location and orientation of the sensor in relation to the fixed frame of reference.

SUMMARY

In Example 1, a sensor assembly includes a first magnetic field sensor that is a first type of sensor and has a first magnetic field sensitivity in a first primary sensing direction. The first primary sensing direction is along a longitudinal axis of the sensor assembly. The sensor assembly further includes a second magnetic field sensor that is a second type of sensor different than the first type of sensor and has a second magnetic field sensitivity in a second primary sensing direction that is less than the first magnetic field sensitivity. The second primary sensing direction is along a second axis that is different than the longitudinal axis.

In Example 2, the sensor assembly of Example 1, wherein the first type of sensor is a giant-magneto-impedance sensor, and wherein the second type of sensor is a magneto-resistive (MR) sensor.

In Example 3, the sensor assembly of any of Examples 1-2, wherein the second magnetic field sensor includes an MR sensing element and at least one flux guide.

In Example 4, the sensor assembly of Example 3, wherein the MR sensing element is one of an anisotropic-magneto-resistive sensing element, giant-magneto-resistive sensing element, tunneling-magneto-resistive sensing element, hall-effect sensing element, colossal magneto-resistive sensing element, extraordinary magneto-resistive sensing element, and spin hall sensing element.

In Example 5, the sensor assembly of any of Examples 1-4, wherein the first magnetic field sensor and the second magnetic field sensors are positioned on a common substrate.

In Example 6, the sensor assembly of Example 1, wherein the wherein the first type of sensor is an inductive sensor, and wherein the second type of sensor is a magneto-resistive (MR) sensor.

In Example 7, the sensor assembly of Example 6, wherein the inductive sensor is an inductive coil sensor.

In Example 8, the sensor assembly of Example 7, wherein the second magnetic field sensor is at least partially positioned within wound coils of the inductive coil sensor.

In Example 9, the sensor assembly of any of Examples 1-8, wherein the second axis is perpendicular to the longitudinal axis.

In Example 10, the sensor assembly of any of claims 1-9, further comprising a third magnetic field sensor that has a third primary sensing direction that is orthogonal to the longitudinal axis and the second axis.

In Example 11, a system includes a magnetic field generator configured to generate a magnetic field and a probe having a longitudinal axis and a sensor assembly positioned at or near a distal end of the probe. The sensor assembly includes a first magnetic field sensor that is a first type of sensor, has a first magnetic field sensitivity, and has a first primary sensing direction along the longitudinal axis. The sensor assembly also includes a second magnetic field sensor that is a second type of sensor different than the first type of sensor, has a second magnetic field sensitivity that is less than the first magnetic field sensitivity, and has a second primary sensing direction along a second axis that is different than the longitudinal axis.

In Example 12, the system of Example 11, wherein the first type of sensor is one of a giant-magneto-impedance sensor and an inductive coil sensor, and wherein the second type of sensor is a magneto-resistive (MR) sensor.

In Example 13, the system of any of Examples 11-12, wherein the second magnetic field sensor includes an MR sensing element that is one of an anisotropic-magneto-resistive sensing element, giant-magneto-resistive sensing element, tunneling-magneto-resistive sensing element, hall-effect sensing element, colossal magneto-resistive sensing element, extraordinary magneto-resistive sensing element, and spin hall sensing element.

In Example 14, the system of any of Examples 11-13, wherein the second axis is perpendicular to the longitudinal axis.

In Example 15, the system of any of Examples 11-14, further comprising a third magnetic field sensor that has a third primary sensing direction that is orthogonal to the longitudinal axis and the second axis.

In Example 16, a sensor assembly including a first magnetic field sensor that is a first type of sensor and has a first magnetic field sensitivity in a first primary sensing direction. The first primary sensing direction is along a longitudinal axis of the sensor assembly. The sensor assembly also includes a second magnetic field sensor that is a second type of sensor different than the first type of sensor and has a second magnetic field sensitivity in a second primary sensing direction that is less than the first magnetic field sensitivity. The second primary sensing direction is along a second axis that is different than the longitudinal axis.

In Example 17, the sensor assembly of Example 16, wherein the first type of sensor is a giant-magneto-impedance sensor, and wherein the second type of sensor is a magneto-resistive (MR) sensor.

In Example 18, the sensor assembly of Example 17, wherein the second magnetic field sensor includes an MR sensing element and at least one flux guide.

In Example 19, the sensor assembly of Example 18, wherein the MR sensing element is one of an anisotropic-magneto-resistive sensing element, giant-magneto-resistive sensing element, tunneling-magneto-resistive sensing element, hall-effect sensing element, colossal magneto-resistive sensing element, extraordinary magneto-resistive sensing element, and spin hall sensing element.

In Example 20, the sensor assembly of Example 16, wherein the first magnetic field sensor and the second magnetic field sensors are positioned on a common substrate.

In Example 21, the sensor assembly of Example 16, wherein the wherein the first type of sensor is an inductive sensor, and wherein the second type of sensor is a magneto-resistive (MR) sensor.

In Example 22, the sensor assembly of Example 21, wherein the inductive sensor is an inductive coil sensor.

In Example 23, the sensor assembly of Example 22, wherein the second magnetic field sensor is at least partially positioned within wound coils of the inductive coil sensor.

In Example 24, the sensor assembly of any of Examples 16-23, wherein the second axis is perpendicular to the longitudinal axis.

In Example 25, the sensor assembly of Example 16, wherein the second type of sensor is one of a Hall sensor or planar coil sensor.

In Example 26, the sensor assembly of Example 25, wherein the first type of sensor is one of a magneto-resistive sensor, a giant-magneto-impedance sensor, and an inductive coil sensor.

In Example 27, the sensor assembly of any of Examples 16-26, further comprising a third magnetic field sensor that has a third primary sensing direction that is orthogonal to the longitudinal axis and the second axis.

In Example 28, a system includes a magnetic field generator configured to generate a magnetic field and a probe having a longitudinal axis and a sensor assembly positioned at or near a distal end of the probe. The sensor assembly includes a first magnetic field sensor that is a first type of sensor, has a first magnetic field sensitivity, and has a first primary sensing direction along the longitudinal axis. The sensor assembly further includes a second magnetic field sensor that is a second type of sensor different than the first type of sensor, has a second magnetic field sensitivity that is less than the first magnetic field sensitivity, and has a second primary sensing direction along a second axis that is different than the longitudinal axis.

In Example 29, the system of Example 28, wherein the first type of sensor is a giant-magneto-impedance sensor, and wherein the second type of sensor is a magneto-resistive (MR) sensor.

In Example 30, the system of Example 28, wherein the first type of sensor is an inductive sensor, and wherein the second type of sensor is a magneto-resistive sensor.

In Example 31, the system of Example 30, wherein the inductive sensor is an inductive coil sensor.

In Example 32, the system of Example 31, wherein the second magnetic field sensor is at least partially positioned within wound coils of the inductive coil sensor.

In Example 33, the system of Example 28, wherein the first type of sensor is one of a magneto-resistive sensor, a giant-magneto-impedance sensor, and an inductive coil sensor, and wherein the second type of sensor is one of a Hall sensor or planar coil sensor.

In Example 34, the system of Example 28, wherein the first type of sensor is a flux-gate sensor, and wherein the second type of sensor is a magneto-resistive sensor.

In Example 35, the system of Example 28, wherein the first magnetic field sensor and the second magnetic field sensors are positioned on a common substrate.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
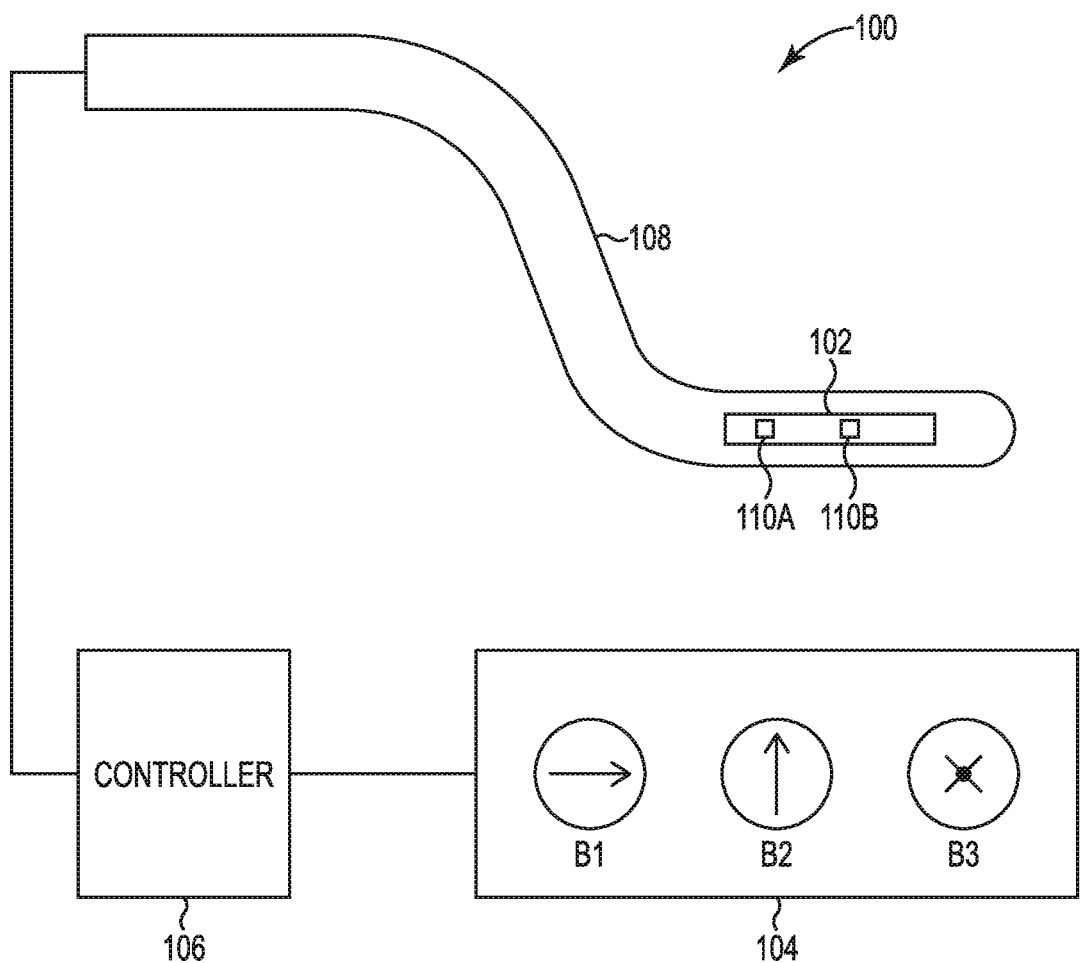
FIG. 1 shows a schematic of a tracking system, in accordance with certain embodiments of the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the invention as defined by the appended claims.

DETAILED DESCRIPTION

During medical procedures, medical devices such as probes (e.g., catheters) are inserted into a patient through the patient's vascular system and/or a catheter lumen. To track the location and orientation of a probe within the patient, probes can be provisioned with magnetic field sensors. As probes become smaller and/or carry more components, the space or real estate available for magnetic field sensors decreases. Certain embodiments of the present disclosure are accordingly directed to systems, methods, and devices including sensor assemblies with compact geometry.

FIG. 1 is a diagram illustrating a tracking system 100 including a sensor assembly 102, magnetic field generator 104, a controller 106, and a probe 108 (e.g., catheter, imaging probe, diagnostic probe). The sensor assembly 102 can be positioned within the probe 108, for example, at a distal end of the probe 108. The tracking system 100 is configured to determine the location and orientation of the sensor assembly 102 and, therefore, the probe 108. Magnetic fields generated by the magnetic field generator 104 provide a frame of reference for the tracking system 100 such that the location and orientation of the sensor assembly 102 is determined relative to the generated magnetic fields. The tracking system 100 can be used in a medical procedure, where the probe 108 is inserted into a patient and the sensor assembly 102 is used to assist with tracking the location of the probe 108 in the patient.

The sensor assembly 102 is communicatively coupled to the controller 106 by a wired or wireless communications path such that the controller 106 sends and receives various signals to and from the sensor assembly 102. The magnetic field generator 104 is configured to generate one or more magnetic fields. For example, the magnetic field generator 104 is configured to generate at least three magnetic fields B1, B2, and B3. Each of the magnetic fields B1, B2, and B3 is directed in a different direction, as indicated by arrows in FIG. 1. Magnetic field B1 is a magnetic field in the horizontal direction, magnetic field B2 is a magnetic field in the vertical direction, and magnetic field B3 is a magnetic field into the page of FIG. 1. The controller 106 is configured to control the magnetic field generator 104 via a wired or wireless communications path to generate one or more of the magnetic fields B1, B2, and B3 for tracking the sensor assembly 102.

The sensor assembly 102 is configured to sense the generated magnetic fields and provide tracking signals indicating the location and orientation of the sensor assembly 102 in up to six degrees of freedom (i.e., x, y, and z measurements, and pitch, yaw, and roll angles). Generally, the number of degrees of freedom that a tracking system is able to track depends on the number of magnetic field sensors and magnetic field generators. For example, a tracking system with a single magnetic field sensor may not be capable of tracking roll angles and thus are limited to tracking in only five degrees of freedom (i.e., x, y, and z coordinates, and pitch and yaw angles). This is because a magnetic field sensed by a single magnetic field sensor does not change as the single magnetic field sensor is "rolled." As such, the sensor assembly 102 includes at least two magnetic field sensors, 110A and 110B. The magnetic field sensors, 110A and 110B, can include sensors such as inductive sensing coils and/or various sensing elements such as magneto-resistive (MR) sensing elements (e.g., anisotropic magneto-resistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or flux-gate sensing elements. In addition, the sensor assembly 102 and/or the probe 108 can feature other types of sensors, such as temperature sensors, ultrasound sensors, etc.

The inventors of the present disclosure have found that certain combinations and arrangements of various types of magnetic field sensors can provide sensor assemblies with compact geometry and/or increased accuracy in sensing magnetic fields. For example, as will be explained in more detail below, certain types of magnetic field sensors are better suited for sensing out-of-plane magnetic fields while others are better suited for sensing in-plane magnetic fields. In addition, certain types of magnetic field sensors provide lower noise and higher sensitivity than certain types of lower-cost or smaller-geometry magnetic field sensors. In addition, certain types of magnetic field sensors, when combined with another type of magnetic field sensor, yield more compact geometry.

The sensor assembly 102 is configured to sense each of the magnetic fields B1, B2, and B3 and provide signals to the controller 106 that correspond to each of the sensed magnetic fields B1, B2, and B3. The controller 106 receives the signals from the sensor assembly 102 via the communications path and determines the position and location of the sensor assembly 102 and probe 108 in relation to the generated magnetic fields B1, B2, and B3.

The magnetic field sensors can be powered by voltages or currents to drive or excite elements of the magnetic field sensors. The magnetic field sensor elements receive the voltage or current and, in response to one or more of the generated magnetic fields, the magnetic field sensor elements generate sensing signals, which are transmitted to the controller 106. The controller 106 is configured to control the amount of voltage or current to the magnetic field sensors and to control the magnetic field generators 104 to generate one or more of the magnetic fields B1, B2, and B3. The controller 106 is configured to receive the sensing signals from the magnetic field sensors and to determine the location and orientation of the sensor assembly 102 (and therefore probe 108) in relation to the magnetic fields B1, B2, and B3. The controller 106 can be implemented using firmware, integrated circuits, and/or software modules that interact with each other or are combined together. For example, the controller 106 may include computer-readable instructions/code for execution by a processor. Such instructions may be stored on a non-transitory computer-readable medium and transferred to the processor for execution. In some embodiments, the controller 106 can be implemented in one or more application-specific integrated circuits and/or other forms of circuitry suitable for controlling and processing magnetic tracking signals and information.

Although the sensor assembly embodiments are described below as being used with a probe, it is appreciated that the sensor assemblies can be utilized in other environments.

Figure 2:
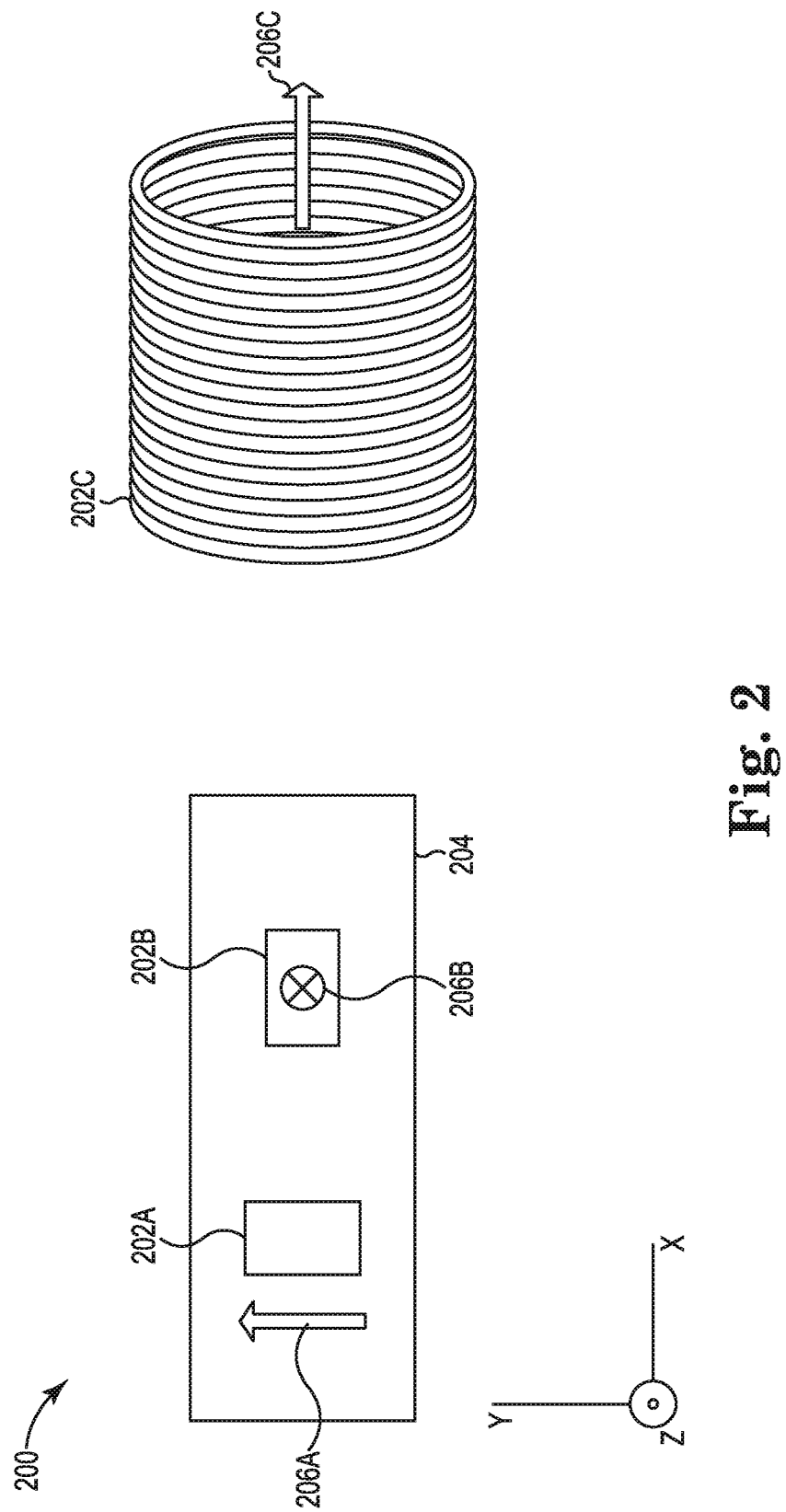
FIG. 2 shows a schematic, exploded view of a sensor assembly, in accordance with certain embodiments of the present disclosure.

FIG. 2 shows an exploded view of a sensor assembly 200 that can be used in tracking systems such as the tracking system 100 of FIG. 1 and positioned in a probe like the probe 108 of FIG. 1. The sensor assembly 200 is shown as having three magnetic field sensors (i.e., a first magnetic field sensor 202A, a second magnetic field sensor 202B, and a third magnetic field sensor 202C), although is appreciated that the sensor assembly 200 could have only two magnetic field sensors or more than three magnetic field sensors. Moreover, the magnetic field sensors 202A-C can be ordered in different arrangements. In some embodiments, the sensor assembly 200 is part of a flex circuit assembly.

The first magnetic field sensor 202A and the second magnetic field sensor 202B can include one or more of various magnetic field sensing elements such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. In some embodiments the first and second magnetic field sensors, 202A and 202B, are different types of sensors, and in other embodiments, the first and second magnetic field sensors, 202A and 202B, are the same type of sensors. In some embodiments, one of the first and second magnetic field sensors, 202A and 202B, is an inductive coil. The magnetic field sensing elements are configured to sense magnetic fields, like those generated by the magnetic field generator 104 of FIG. 1, and generate a responsive sensing signal. The first and second magnetic field sensors, 202A and 202B, can also include components such as substrates and flux guides. The first magnetic field sensor 202A and the second magnetic field sensor 202B are shown being positioned on a common sensor assembly substrate 204, which can form part of a flex circuit.

FIG. 2 features an arrow 206A pointing along a Y-axis and positioned next to the first magnetic field sensor 202A. The arrow 206A represents a primary magnetic field sensing direction of the first magnetic field sensor 202A. In other words, the first magnetic field sensor is oriented and configured such that it senses magnetic fields along the Y-axis. Arrow 206B is pointing into the page and represents a primary magnetic field sensing direction of the second magnetic field sensor 202B. In other words, the second magnetic field sensor is oriented and configured such that it senses magnetic fields along the Z-axis, which is orthogonal to the Y-axis. It appreciated that each of the magnetic field sensors can be capable of sensing magnetic fields in other directions too.

The third magnetic field sensor 202C is shown in FIG. 2 as being an inductive coil. The third magnetic field sensor 202C is configured to sense magnetic field components in the X-axis as indicated by arrow 206C, which is the third magnetic field sensor's primary magnetic field sensing direction. The coil 202C can be wound to form a hollow cylinder-like shape. When assembled, the first and second magnetic field sensors, 202A and 202B, can be fully or partially positioned within the coil 202C. Such an arrangement provides a sensor assembly with compact geometry and that is able to sense magnetic fields in a plurality of directions. In some embodiments, the first magnetic field sensor 202A, the second magnetic field sensor 202B, and the common sensor assembly substrate 204 are encapsulated by and coupled to the coil 202C with an epoxy.

Further, when the sensor assembly 200 is positioned within a probe, such as a catheter, the coil 202C can take advantage of the geometry of the probe in that the coil 202C can be designed to extend along a longitudinal axis of a probe which is an axis that provides the most space. A coil 202C that is longer and/or includes more windings can result in better sensitivity compared to the other magnetic field sensors, including coils that are shorter and/or have fewer windings. As such, the third magnetic field sensor 202C can be characterized as having a greater sensitivity to magnetic fields than the first and second magnetic field sensors' sensitivity. In other words, for a given magnetic field amplitude, the third magnetic field sensor 202C generates a larger responsive sensing signal, which is used to determine location and orientation of the sensor assembly 200.

The increased sensitivity of the third magnetic field sensor 202C relative to the sensitivity of the other magnetic field sensors increases sensing performance of the overall sensor assembly 200. As mentioned above, a single sensor can be configured to sense up to five degrees of freedom (i.e., x, y, z, pitch, and yaw). Because the third magnetic field sensor 202C is more sensitive than the other magnetic field sensors of the sensor assembly 200, the sensed signals generated by the third magnetic field sensor 202C can dominate the sensed signals generated by the other magnetic field sensors. As such, the sensitivity of the first and second magnetic field sensors, 202A and 202B, need not be as sensitive as the third magnetic field sensor 202C and therefore can be made smaller, which can reduce the overall size of the sensor assembly 200 and/or may be cheaper magnetic field sensors. In some embodiments, the more sensitive magnetic field sensor can be two to ten times more sensitive than the other magnetic field sensors. In some embodiments, the more sensitive magnetic field sensor can be up to five times more sensitive than the other magnetic field sensors. The sensing signals generated by the magnetic field sensors 202A-C can be transmitted from the sensing assembly 200 to a controller, such as the controller 106 of FIG. 1, wirelessly or via one or more conductors.

Figure 3:
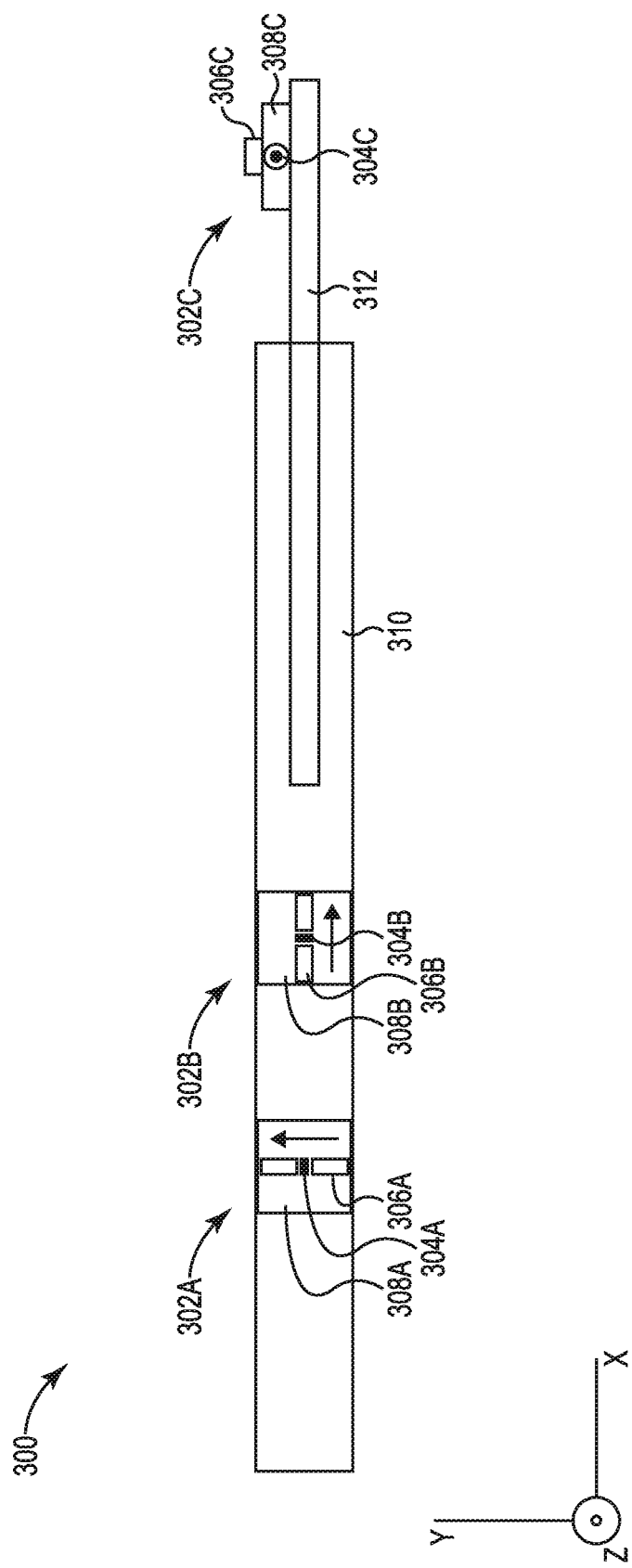
FIG. 3 shows a cut-away schematic of a probe, in accordance with certain embodiments of the present disclosure.

FIG. 3 shows a schematic of a sensor assembly 300 that can be used in tracking systems such as the tracking system 100 of FIG. 1 and positioned in a probe like the probe 108 of FIG. 1. The sensor assembly 300 is shown being positioned at a distal end of a probe 301, like the probe 108 of FIG. 1. The sensor assembly 300 is shown as having three magnetic field sensors (i.e., a first magnetic field sensor 302A, a second magnetic field sensor 302B, and a third magnetic field sensor 302C), although is appreciated that the sensor assembly 300 could have only two magnetic field sensors or more than three magnetic field sensors. Moreover, the magnetic field sensors 302A-C can be ordered in different arrangements. In some embodiments, the sensor assembly 300 is part of a flex circuit assembly.

The first magnetic field sensor 302A, the second magnetic field sensor 302B, and the third magnetic field sensor 302C can include one or more of various magnetic field sensing elements, 304A, 304B, and 304C, such as MR sensing elements (e.g., AMR sensing elements, GMR sensing elements, TMR sensing elements, Hall effect sensing elements, CMR sensing elements, EMR sensing elements, spin Hall sensing elements, and the like), GMI sensing elements, and/or flux-gate sensing elements. In some embodiments the first, second, and third magnetic field sensors, 302A, 302B, and 302C, are different types of sensors. The magnetic field sensing elements are configured to sense magnetic fields, like those generated by the magnetic field generator 104 of FIG. 1, and generate a responsive sensing signal.

Each magnetic field sensor can include magnetic field sensor components, 306A, 306B, and 306C, such as flux guides, which direct magnetic flux towards MR sensing elements. The first magnetic field sensor 302A includes a first sensor substrate 308A, the second magnetic field sensor 302B includes a second sensor substrate 308B, and the third magnetic field sensor 302C includes a third sensor substrate 308C. The first magnetic field sensor 302A and the second magnetic field sensor 302B are shown being positioned on a common sensor assembly substrate 310, which can form part of a flex circuit. The third magnetic field sensor 302C is shown being positioned on another sensor assembly substrate 312, which is coupled to the common sensor assembly substrate 310, is oriented perpendicular to the common sensor assembly substrate 310, and can form part of a flex circuit.

FIG. 3 features an arrow 314A pointing along a Y-axis and positioned next to the first magnetic field sensor 302A. The arrow 314A represents a primary magnetic field sensing direction of the first magnetic field sensor 302A. In other words, the first magnetic field sensor is oriented such that it senses magnetic fields along the Y-axis. Arrow 306B is pointing along the X-direction and represents a primary magnetic field sensing direction of the second magnetic field sensor 302B. In other words, the second magnetic field sensor 302B is oriented such that it senses magnetic fields along the X-axis. Arrow 306C is pointing into the page and represents a primary magnetic field sensing direction of the third magnetic field sensor 302C. In other words, the third magnetic field sensor 302C is oriented such that it senses magnetic fields along the Z-axis, which is orthogonal to the Y-axis. It appreciated that each of the magnetic field sensors can be capable of sensing magnetic fields in other directions too.

In some embodiments, the first and third magnetic field sensors, 302A and 302C, are MR-type sensors, which include MR sensing elements, while the second magnetic field sensor 302B is an inductive sensor such as a GM I-type sensor with GMI sensing elements. GMI sensors have lower noise and higher sensitivity than certain MR sensors, such as GMR sensors.

In some embodiments, the first and third magnetic field sensors, 302A and 302C, are MR-type sensors, while the second magnetic field sensor 302B is a flux-gate-type sensor. Like GMI sensors, flux-gate-type sensors have lower noise and higher sensitivity than certain MR sensors, such as GMR sensors.

In some embodiments, the first and third magnetic field sensors, 302A and 302C, are either MR-type or GMI-type sensors, while the second magnetic field sensor 302B is an inductive coil. MR and GMI sensors are generally more compact than inductive coils and can provide greater sensitivity in a more compact space compared to inductive coils.

As such, in the embodiments described above, the second magnetic field sensor 302B can be characterized as having a greater sensitivity to magnetic fields than the first and third magnetic field sensors' sensitivity. In other words, for a given magnetic field amplitude, the second magnetic field sensor 302B generates a larger responsive sensing signal, which is used to determine location and orientation of the sensor assembly 300. The increased sensitivity of the second magnetic field sensor 302B relative to the sensitivity of the other magnetic field sensors increases sensing performance of the overall sensor assembly 300.

As mentioned above, a single sensor can be configured to sense up to five degrees of freedom (i.e., x, y, z, pitch, and yaw). Because the second magnetic field sensor 302B is more sensitive than the other magnetic field sensors of the sensor assembly 300, the sensed signals generated by the second magnetic field sensor 302B can dominate the sensed signals generated by the other magnetic field sensors. As such, the sensitivity of the first and third magnetic field sensors, 302A and 302C, need not be as sensitive as the second magnetic field sensor 302B and therefore can be made smaller, which can reduce the overall size of the sensor assembly 300, and/or may be cheaper magnetic field sensors. In some embodiments, the more sensitive magnetic field sensor can be two to ten times more sensitive than the other magnetic field sensors. In some embodiments, the more sensitive magnetic field sensor can be up to five times more sensitive than the other magnetic field sensors.

In some embodiments, the first and third magnetic field sensors, 302A and 302C, are Hall-type sensors and/or planar coil-type sensors, while the second magnetic field sensor 302B is an MR-type, GMI-type, or an elongated inductive coil-type sensor. Hall sensors and planar coils can provide greater sensitivity to out-of-plane magnetic fields given the compact space of a probe.

It should be noted that, for simplicity and ease of understanding, the elements described above and shown in the figures are not drawn to scale and may omit certain features. As such, the drawings do not necessarily indicate the relative sizes of the elements or the non-existence of other features.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A sensor assembly comprising:
    a first magnetic field sensor that is an inductive coil sensor and has a first magnetic field sensitivity in a first primary sensing direction, wherein the first primary sensing direction is along a longitudinal axis of the sensor assembly; and
    a second magnetic field sensor that is a magneto-resistive (MR) sensor and has a second magnetic field sensitivity in a second primary sensing direction that is less than the first magnetic field sensitivity, wherein the second primary sensing direction is along a second axis that is different than the longitudinal axis.

2. The sensor assembly of claim 1, wherein the second magnetic field sensor includes an MR sensing element and at least one flux guide.

3. The sensor assembly of claim 2, wherein the MR sensing element is one of an anisotropic-magneto-resistive sensing element, giant-magneto-resistive sensing element, tunneling-magneto-resistive sensing element, hall-effect sensing element, colossal magneto-resistive sensing element, extraordinary magneto-resistive sensing element, and spin hall sensing element.

4. The sensor assembly of claim 1, wherein the first magnetic field sensor and the second magnetic field sensors are positioned on a common substrate.

5. The sensor assembly of claim 1, wherein the second magnetic field sensor is at least partially positioned within wound coils of the inductive coil sensor.

6. The sensor assembly of claim 1, wherein the second axis is perpendicular to the longitudinal axis.

7. The sensor assembly of claim 1, further comprising:
    a third magnetic field sensor that has a third primary sensing direction that is orthogonal to the longitudinal axis and the second axis.

8. The sensor assembly of claim 1, wherein the first magnetic field sensitivity is two to ten times as sensitive as the second magnetic field sensitivity.

9. The sensor assembly of claim 1, wherein the first magnetic field sensitivity is up to five times as sensitive as the second magnetic field sensitivity.

10. A system comprising:
    a probe having a first longitudinal axis and a sensor assembly positioned at or near a distal end of the probe and having a second longitudinal axis aligned with the first longitudinal axis, the sensor assembly including:
        a first magnetic field sensor that is a first type of sensor being an inductive coil sensor, that has a first magnetic field sensitivity, and that has a first primary sensing direction along the second longitudinal axis; and
        a second magnetic field sensor that is a second type of sensor being a magneto-resistive sensor sensor, that has a second magnetic field sensitivity that is less than the first magnetic field sensitivity, and that has a second primary sensing direction along a second axis that is different than the second longitudinal axis.

11. The system of claim 10, wherein the second magnetic field sensor is at least partially positioned within wound coils of the inductive coil sensor.

12. The system of claim 10, wherein the first magnetic field sensor and the second magnetic field sensors are positioned on a common substrate.

13. The sensor assembly of claim 10, wherein the first magnetic field sensitivity is two to ten times as sensitive as the second magnetic field sensitivity.

14. The sensor assembly of claim 10, wherein the first magnetic field sensitivity is up to five times as sensitive as the second magnetic field sensitivity.

15. The system of claim 10, further comprising a magnetic field generator configured to generate a magnetic field.

16. A sensor assembly comprising:
    a flux-gate sensor having a first magnetic field sensitivity in a first primary sensing direction, which is along a longitudinal axis of the sensor assembly; and
    a magneto-resistive (MR) sensor having a second magnetic field sensitivity in a second primary sensing direction that is less than the first magnetic field sensitivity, wherein the second primary sensing direction is along a second axis that is different than the longitudinal axis.

17. The sensor assembly of claim 16, wherein the first magnetic field sensitivity is two to ten times as sensitive as the second magnetic field sensitivity.

18. The sensor assembly of claim 16, wherein the first magnetic field sensitivity is up to five times as sensitive as the second magnetic field sensitivity.

* * * * *